US010881821B2

(12) United States Patent
Truschel et al.

(10) Patent No.: US 10,881,821 B2
(45) Date of Patent: Jan. 5, 2021

(54) MECHANICAL VENTILATION BASED ON ALVEOLAR VENTILATION

(71) Applicant: KONINKLIJKE PHILIPS N.V., Eindhoven (NL)

(72) Inventors: William Anthony Truschel, Oakmont, PA (US); Joshua Scott Snyder, McMurray, PA (US)

(73) Assignee: Koninklijke Philips N.V., Eindhoven (NL)

(*) Notice: Subject to any disclaimer, the term of this patent is extended or adjusted under 35 U.S.C. 154(b) by 682 days.

(21) Appl. No.: 15/584,635

(22) Filed: May 2, 2017

(65) Prior Publication Data

US 2018/0318532 A1    Nov. 8, 2018

Related U.S. Application Data

(60) Provisional application No. 62/331,024, filed on May 3, 2016.

(51) Int. Cl.
*A61M 16/00* (2006.01)

(52) U.S. Cl.
CPC . *A61M 16/0069* (2014.02); *A61M 2016/0027* (2013.01); *A61M 2016/0036* (2013.01);
(Continued)

(58) Field of Classification Search
CPC ...... A61M 16/0069; A61M 2016/0027; A61M 2016/0036; A61M 2205/3306;
(Continued)

(56) References Cited

U.S. PATENT DOCUMENTS 6,599,252 B2 * 7/2003 Starr ............... A61B 5/091 600/532
6,648,832 B2 * 11/2003 Orr ............... A61B 5/029 128/204.21

(Continued)

FOREIGN PATENT DOCUMENTS

EP    1985326 B9    1/2012
UA    70974 U    6/2012

OTHER PUBLICATIONS

Brewer L.M. et al., "Anatomic Dead Space Cannot Be Predicted by Body Weight", Respiratory Care, Jul. 2008, vol. 53, No. 7, pp. 885-891.

(Continued)

*Primary Examiner* — Rachel T Sippel
(74) *Attorney, Agent, or Firm* — Daniel H. Brean

(57) ABSTRACT

The present disclosure pertains to a mechanical ventilator system configured to control a pressurized flow of breathable gas for delivery to a subject based on alveolar ventilation of the subject. The mechanical ventilator system comprises a pressure generator configured to generate the pressurized flow of breathable gas for delivery to the subject, the pressure generator configured to control one or more ventilation parameters of the pressurized flow of breathable gas according to a prescribed mechanical ventilation therapy regime; one or more sensors configured to generate output signals conveying information related to the alveolar ventilation of the subject; and one or more hardware processors configured by machine-readable instructions to: determine the alveolar ventilation of the subject based on the output signals; and cause the pressure generator to adjust the one or more ventilation parameters of the pressurized flow of breathable gas based on the determined alveolar ventilation.

12 Claims, 5 Drawing Sheets

(52) U.S. Cl.
CPC .............. *A61M 2205/3306* (2013.01); *A61M 2205/3334* (2013.01); *A61M 2205/3375* (2013.01); *A61M 2230/42* (2013.01); *A61M 2230/432* (2013.01)

(58) Field of Classification Search
CPC .. A61M 2205/3334; A61M 2205/3375; A61M 2230/42; A61M 2230/432
See application file for complete search history.

(56) References Cited

U.S. PATENT DOCUMENTS

| | | | |
|---|---|---|---|
| 2010/0132710 A1* | 6/2010 | Orr ........................ | A61B 5/029 128/205.17 |
| 2010/0300445 A1* | 12/2010 | Chatburn .......... | A61M 16/0063 128/204.23 |
| 2013/0006134 A1* | 1/2013 | Doyle .................. | A61B 5/0836 600/532 |
| 2015/0231351 A1* | 8/2015 | Jonson .................. | A61B 5/087 128/204.22 |

OTHER PUBLICATIONS

Kiiski et al., "Measurement of Alveolar Ventilation and Changes in Deadspace by Indirect Calorimetry During Mechanical Ventilation: A Laboratory and Clinical Validation", Critical Care Medicine. 19(10):1303-1309, Oct. 1991.

* cited by examiner

MECHANICAL VENTILATION BASED ON ALVEOLAR VENTILATION

CROSS-REFERENCE TO RELATED APPLICATIONS

This patent application claims the priority benefit under 35 U.S.C. § 119(e) of U.S. Provisional Application No. 62/331,024 filed on May 3, 2016, the contents of which are herein incorporated by reference.

BACKGROUND OF THE INVENTION

Field of the Invention

The present disclosure pertains to a method and a mechanical ventilator system for controlling a pressurized flow of breathable gas for delivery to a subject based on alveolar ventilation of the subject.

Description of the Related Art

A mechanical ventilator assists breathing by pushing air into a patient's lungs. Ventilators may operate under different control modes. One control mode is a volume control mode wherein the ventilator delivers a prescribed volume of air to the patient. Typically, the volume controlled in the volume control mode is a tidal volume.

SUMMARY OF THE INVENTION

Accordingly, one or more aspects of the present disclosure relate to a mechanical ventilator system configured to control a pressurized flow of breathable gas for delivery to a subject based on alveolar ventilation of the subject. The mechanical ventilator system comprises a pressure generator configured to generate the pressurized flow of breathable gas for delivery to the subject, the pressure generator configured to control one or more ventilation parameters of the pressurized flow of breathable gas according to a prescribed mechanical ventilation therapy regime; one or more sensors configured to generate output signals conveying information related to the alveolar ventilation of the subject; and one or more hardware processors configured by machine-readable instructions to: determine the alveolar ventilation of the subject based on the output signals; and cause the pressure generator to adjust the one or more ventilation parameters of the pressurized flow of breathable gas based on the determined alveolar ventilation.

Another aspect of the present disclosure relates to a method for controlling a pressurized flow of breathable gas for delivery to a subject with a mechanical ventilator system based on alveolar ventilation of the subject. The mechanical ventilator system comprises a pressure generator, one or more sensors, one or more hardware processors, and/or other components. The method comprises: generating, with the pressure generator, the pressurized flow of breathable gas for delivery to the subject; controlling, with the pressure generator, one or more ventilation parameters of the pressurized flow of breathable gas according to a prescribed mechanical ventilation therapy regime; generating, with the one or more sensors, output signals conveying information related to the alveolar ventilation of the subject; determining, with the one or more hardware processors, the alveolar ventilation of the subject based on the output signals; and causing, with the one or more hardware processors, the pressure generator to adjust the one or more ventilation parameters of the pressurized flow of breathable gas based on the determined alveolar ventilation.

Still another aspect of the present disclosure relates to a mechanical ventilator system configured to control a pressurized flow of breathable gas for delivery to a subject based on alveolar ventilation of the subject. The mechanical ventilator system comprises: means for generating the pressurized flow of breathable gas for delivery to the subject, the means for generating the pressurized flow of breathable gas configured to control one or more ventilation parameters of the pressurized flow of breathable gas according to a prescribed mechanical ventilation therapy regime; means for generating output signals conveying information related to the alveolar ventilation of the subject; means for determining the alveolar ventilation of the subject based on the output signals; and means for causing the means for generating the pressurized flow of breathable gas to adjust the one or more ventilation parameters of the pressurized flow of breathable gas based on the determined alveolar ventilation.

These and other features and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
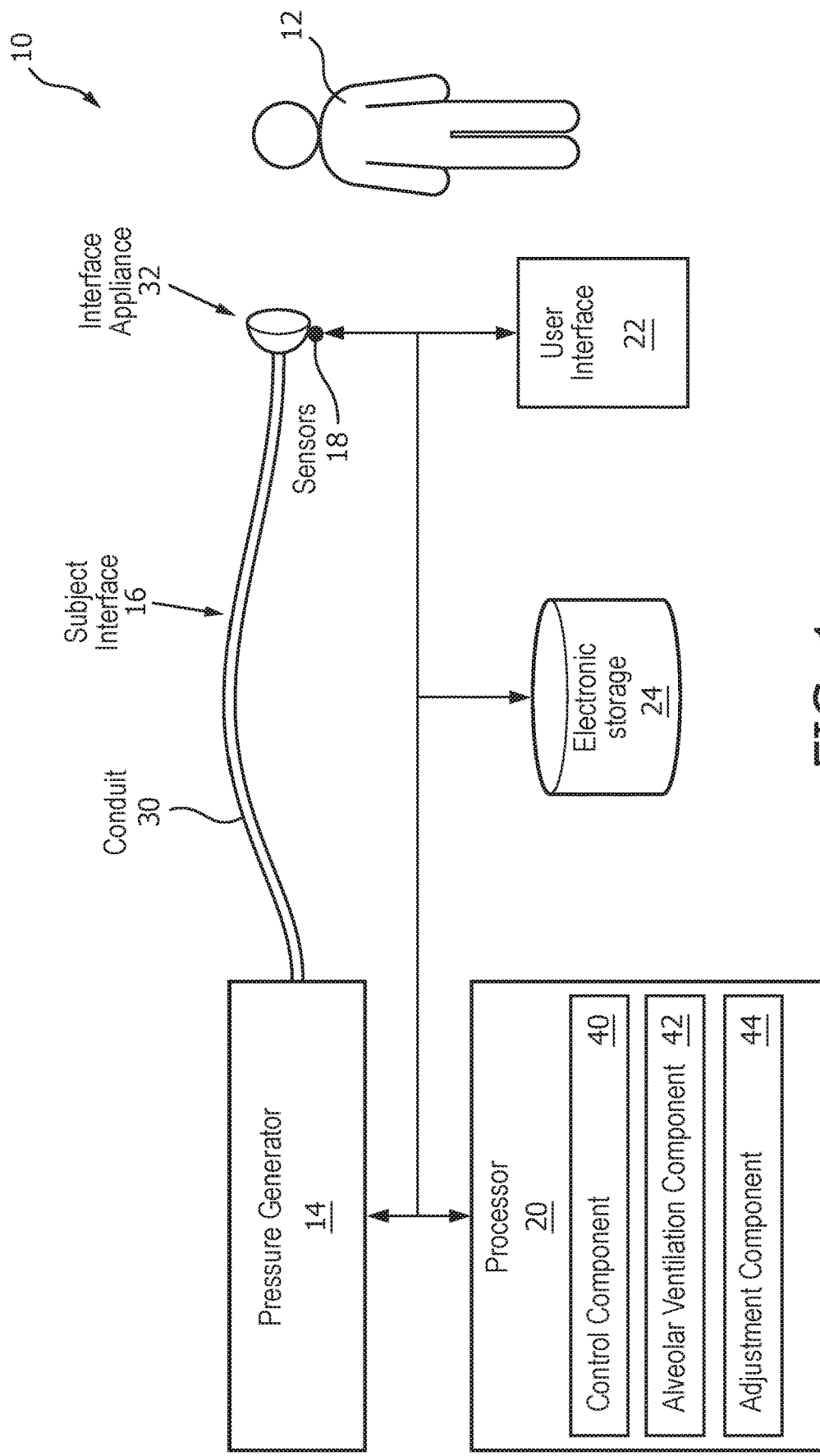
FIG. 1 is a schematic illustration of a mechanical ventilator system configured to control a pressurized flow of breathable gas for delivery to a subject based on alveolar ventilation of the subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a mechanical ventilator system 10 configured to control a pressurized flow of breathable gas for delivery to a subject 12 based on alveolar ventilation of subject 12. One or more parameters of the pressurized flow of breathable gas are controlled to mechanically ventilate subject 12. This may include providing mechanical ventilation to assist subject 12 as subject 12 attempts to breathe for himself System 10 is configured to deliver mechanical ventilation pressure support using a measurement of anatomic dead space in order to more accurately monitor and control alveolar ventilation. System 10 uses a flow rate of the pressurized flow of breathable gas and carbon dioxide ($CO_2$) concentration information in a signal from a capnography sensor to determine alveolar ventilation of subject 12 and an appropriate level of ventilation required for respiratory support based on the determined alveolar ventilation.

Advantageously, system 10 facilitates normalizing mechanical ventilator settings when a subject interface used with the mechanical ventilator varies from a full face mask (and/or other non-invasive interfaces) to an endotracheal and/or tracheostomy tube (and/or other invasive interfaces). Respiration causes gas exchange at the alveolar level in a subject. However, typical mechanical ventilators deliver tidal volume controlled ventilation to a subject airway that includes but exceeds an alveolar space in the subject. The ventilator delivers this ventilation through a variety of invasive or non-invasive interfaces. When non-invasive interfaces are used, the tidal ventilation for one breath is significantly greater than the tidal ventilation at the alveolar blood barrier. When invasive interfaces are used (e.g., an endotracheal or tracheostomy tube), the anatomical space occupied by the oro-nasal cavity is bypassed and the alveolar ventilation quantity is nearer to the alveolar ventilation as compared to the non-invasive interface. Mechanical ventilators are typically used with both invasive and non-invasive interfaces and the ventilator settings and/or protocols for tidal volume assessment are not typically adjusted based on the interface. Tidal volume controlled ventilation further neglects the level of alveolar recruitment achieved by extrinsic and/or intrinsic end expiratory pressure. Greater alveolar recruitment translates to greater alveolar ventilation, but tidal ventilation measurement neglects the significance of alveolar recruitment.

System 10 is configured such that, through the use of capnography based on optical sensor output signals from an optical sensor positioned near the subject interface and/or other information (e.g., as described below), the alveolar ventilation of subject 12 is determined on a breath-by-breath basis and/or at other times. System 10 is configured such that the mechanical ventilation is controlled based on the determined alveolar ventilation and the respiratory therapy is adjusted to achieve a set alveolar ventilation rather than a set tidal ventilation. This overcomes the difficulty of titrating mechanical ventilation settings based on the variable interface, variable anatomical dead space, and variable alveolar recruitment in different subjects. System 10 adjusts mechanical ventilation therapy in response to changes in alveolar ventilation to achieve substantially consistent gas exchange at the alveolar level. In some embodiments, system 10 comprises one or more of a pressure generator 14, a subject interface 16, one or more sensors 18, one or more processors 20, a user interface 22, electronic storage 24, and/or other components.

Pressure generator 14 is configured to generate a pressurized flow of breathable gas for delivery to the airway of subject 12. Pressure generator 14 may control one or more ventilation parameters of the flow of gas (e.g., rates, pressures, volumes, temperatures, compositions, etc.) for therapeutic purposes, and/or for other purposes. Pressure generator 14 is configured to control one or more ventilation parameters of the pressurized flow of breathable gas according to a prescribed mechanical ventilation therapy regime and/or other therapy regimes. By way of a non-limiting example, pressure generator 14 may be configured to control a breath rate, a flow rate, a pressure support positive end expiratory pressure (PEEP), a tidal volume, a minute volume, an inspiratory to expiratory breath phase ratio (e.g., an I:E ratio), and/or other ventilation parameters of the flow of gas to provide a suitable alveolar ventilation.

Pressure generator 14 receives a flow of gas from a gas source, such as the ambient atmosphere, and elevates and/or reduces the pressure of that gas for delivery to the airway of subject 12. Pressure generator 14 is and/or includes any device, such as, for example, a pump, blower, piston, or bellows, that is capable of elevating and/or reducing the pressure of the received gas for delivery to a patient. Pressure generator 14 may comprise servo controlled valves and/or motors, one or more other valves and/or motors for controlling the pressure and/or flow of gas, and/or other components that will contribute to either an increase or a decrease in alveolar ventilation. The present disclosure also contemplates controlling the operating speed of the blower, either alone or in combination with such valves, to control the pressure and/or flow of gas provided to the patient.

Subject interface 16 is configured to deliver the pressurized flow of breathable gas to the airway of subject 12. As such, subject interface 16 comprises conduit 30, interface appliance 32, and/or other components. Conduit 30 is configured to convey the pressurized flow of gas to interface appliance 32. Conduit 30 may be a flexible length of hose, or other conduit that places interface appliance 32 in fluid communication with pressure generator 14. Interface appliance 32 is configured to deliver the flow of gas to the airway of subject 12. In some embodiments, interface appliance 32 is non-invasive. As such, interface appliance 32 non-invasively engages subject 12. Non-invasive engagement comprises removably engaging an area (or areas) surrounding (e.g., not inside) one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance, including an invasive interface appliance such as an endotracheal tube and/or other appliances.

Sensors 18 are configured to generate output signals conveying information related to the alveolar ventilation of subject 12 and/or other gas and/or breathing parameters. In some embodiments, the information related to the alveolar ventilation of subject 12 includes the flow rate (and/or information related to the flow rate) of the pressurized flow of breathable gas, the $CO_2$ concentration (and/or information related to the $CO_2$ concentration such as the partial pressure of $CO_2$ and/or other information) in the pressurized flow of breathable gas, and/or other information. In some embodiments, the information related to other gas and/or breathing parameters may comprise information related to volumes (e.g., tidal volume, minute volume, etc.), pressures (e.g., inhalation pressure, exhalation pressure, etc.), other compositions (e.g., concentration(s)) of one or more constituent gasses, a gas temperature, a gas humidity, acceleration, velocity, acoustics, changes in a parameter indicative of respiratory effort by subject 12, and/or other parameters.

Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. For example, one or more of sensors 18 may generate an output based on an operating parameter of pressure generator 14 (e.g., a valve driver or motor current, voltage, rotational velocity, and/or other operating parameters). Although sensors 18 are illustrated at a single location within (or in communication with) conduit 30 between interface appliance 32 and pressure generator 14, this is not intended to be limiting. Sensors 18 may include sensors disposed in a plurality of locations, such as for example, within pressure generator 14, within (or in communication with) interface appliance 32, in communication with subject 12, and/or in other locations. For example, sensors 18 may include a flow rate sensor, a capnography sensor (configured to generate output signals conveying information related to a concentration of $CO_2$ in the pressurized flow of breathable gas), a volume sensor, a pressure sensor, a temperature sensor, an acoustic sensor, and/or other sensors located at various locations in system 10. In some embodiments, the capnography sensor may comprise an optical sensor positioned at or near interface appliance 32 for example.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program components. The one or more computer program components may comprise one or more of a control component 40, an alveolar ventilation component 42, an adjustment component 44, and/or other components. Processor 20 may be configured to execute components 40, 42, and/or 44 by software; hardware; firmware; some combination of software, hardware, and/or firmware; and/or other mechanisms for configuring processing capabilities on processor 20.

It should be appreciated that although components 40, 42, and 44 are illustrated in FIG. 1 as being co-located within a single processing unit, in implementations in which processor 20 comprises multiple processing units, one or more of components 40, 42, and/or 44 may be located remotely from the other components. The description of the functionality provided by the different components 40, 42, and/or 44 described below is for illustrative purposes, and is not intended to be limiting, as any of components 40, 42, and/or 44 may provide more or less functionality than is described. For example, one or more of components 40, 42, and/or 44 may be eliminated, and some or all of its functionality may be provided by other components 40, 42, and/or 44. As another example, processor 20 may be configured to execute one or more additional components that may perform some or all of the functionality attributed below to one of components 40, 42, and/or 44.

Control component 40 is configured to control pressure generator 14 to generate the pressurized flow of breathable gas. Control component 40 is configured to cause pressure generator 14 to generate the pressurized flow of breathable gas in accordance with a prescribed mechanical ventilation therapy regime. Control component 40 is configured to cause pressure generator 14 to control the one or more ventilation parameters of the pressurized flow of breathable gas (e.g., described above) according to the prescribed mechanical ventilation therapy regime. Control component 40 is configured to control pressure generator 14 based on information related to the output signals from sensors 18, information determined by alveolar ventilation component 42 and/or adjustment component 44, information entered and/or selected by a user via user interface 22, and/or other information.

The pressurized flow of gas generated by pressure generator 14 is controlled to replace and/or compliment the regular breathing of subject 12. Airway ventilation therapy may be used to maintain an open airway in subject 12 so that oxygen and carbon dioxide may be exchanged more easily, requiring little and/or no effort from subject 12 in order to facilitate gas exchange. Airway ventilation therapy may be pressure limited to prevent cardiac restriction and encourage circulation ejection to improve gas exchange. In some embodiments, control component 40 may be configured to control pressure generator 14 to generate the flow of gas in accordance with a ventilation and/or positive airway pressure support therapy regime in addition to and/or instead of a mechanical ventilation therapy regime. By way of non-limiting example, control component 40 may control pressure generator 14 such that the pressure support provided to subject 12 via the flow of gas comprises continuous positive airway pressure support (variable CPAP), variable bi-level positive airway pressure support (BPAP), proportional positive airway pressure support (PPAP), and/or other types of pressure support therapy in order to maintain a suitable alveolar ventilation.

Alveolar ventilation component 42 is configured to determine the alveolar ventilation of subject 12. Alveolar ventilation component 42 is configured to determine the alveolar ventilation of subject 12 based on the output signals from sensors 18 and/or other information. In some embodiments, determining the alveolar ventilation of subject 12 based on the output signals includes determining an exhaled volumetric flow of $CO_2$ based on the flow rate information and the $CO_2$ concentration information, and integrating the exhaled volumetric flow of $CO_2$ during an expiratory phase of subject 12.

In some embodiments, to determine the alveolar ventilation of subject 12, alveolar ventilation component 42 receives the flow rate information, the $CO_2$ concentration information (e.g., the partial pressure of $CO_2$), and/or other information from sensors 18 and synchronizes the flow rate information and the CO₂ concentration information. Alveolar ventilation component 42 may synchronize the flow rate information and the CO₂ concentration information with a deconvolution algorithm to reduce and/or eliminate effects of sensor delay and/or for other reasons, for example. As specific information regarding the sensors is known or characterized, a deconvolution algorithm serves to ensure that effects of the measurement techniques in terms of delay are reversed by a mathematical formula. In this sense, the sensors are synchronized to compare the correct concentration for any instantaneous flow measurement. The deconvolution uses a boxcar function with a set width to take an average of points before and after the current point being calculated. By way of a non-limiting example, FIG. 2 illustrates synchronized flow rate 200 and CO₂ concentration 202 (CO₂ partial pressure) graph.

Figure 2:
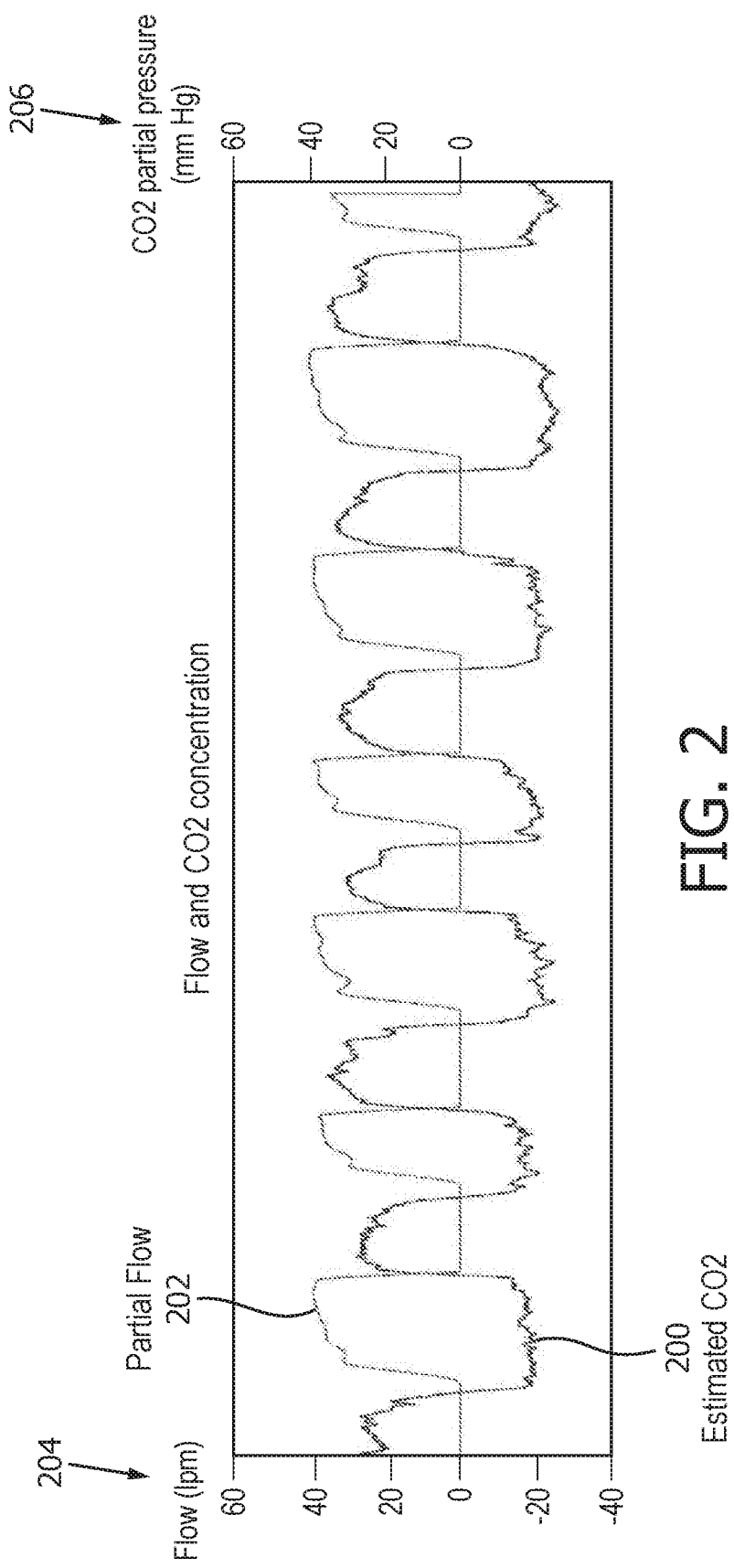
FIG. 2 illustrates a graph of flow rate and carbon dioxide concentration.

In FIG. 2, flow rate 200 is illustrated in units 204 of liters per minute (lpm) and CO₂ is illustrated in units 206 of (mmHg). The CO₂ concentration 202 is shown going almost immediately to 0 mmHg as the flow rate 200 becomes increasingly positive (inhalation). The small gap between the two accounts for the slight amount of CO₂ left in subject interface 16 (shown in FIG. 1, for example). Also, the period of time between the flow rate 200 going negative and CO₂ concentration 202 going positive is a visual indicator of alveolar dead space.

Returning to FIG. 1, after the flow rate information and the CO₂ concentration information is synchronized, the CO₂ concentration information (e.g., which includes the partial pressure of CO₂) is used to determine a CO₂ percentage at time t according to Equation 1.

$$CO_2\%(t) = \frac{P_{CO_2}(t)}{P_{atm}} \quad [1]$$

In Equation 1, $CO_2\%$ (t) represents the percentage of $CO_2$ in the pressurized flow of breathable gas from subject 12, $P_{CO2}(t)$ is the partial pressure of $CO_2$ determined based on the output signals of a capnography sensor (one of sensors 18), and $P_{atm}$ is the atmospheric pressure (e.g., determined based on the output signals of another one of sensors 18).

Volumetric flow of CO₂ is given by Equation 2.

$$Q_{CO_2}(t) = Q_P(t) \frac{CO_2\%(t)}{ETCO_2\%(\text{breath})} \quad [2]$$

In Equation 2, $Q_{CO2}$ (t) is the exhaled volumetric flow of $CO_2$ (described above), $Q_p$ (t) is the flow rate of the pressurized flow of breathable gas in the airway of subject 12, and $ETCO_2\%$ (breath) is the maximum value of $CO_2\%$ during a breath (e.g., determined by alveolar ventilation component 42 over one breath based on Equation 1). Alveolar ventilation component 42 is configured such that alveolar ventilation is then given by the integral of $Q_{CO2}$ during an expiratory phase of a breath of subject 12 as shown in Equation 3.

$$v_{alveolar}(\text{breath}) = \int_{expiration} Q_{CO2}(t) \cdot dt \quad [3]$$

In some embodiments, alveolar ventilation component 42 is configured to determine one or more gas parameters of the pressurized flow of breathable gas and/or breathing parameters of subject 12 in addition to and/or instead of determining the alveolar ventilation of subject 12. The alveolar ventilation, the one or more gas parameters, the one or more breathing parameters, and/or other information may be determined based on the output signals from sensors 18 and/or other information. The alveolar ventilation, the one or more gas parameters, the one or more breathing parameters, and/or other information may be determined one or more (e.g., multiple) times per inhalation and/or exhalation of subject 12. In some embodiments, the alveolar ventilation, one or more of the gas parameters, one or more of the breathing parameters, and/or other information may be determined at regular time intervals during an inhalation and/or an exhalation of subject 12 and/or at other times. The alveolar ventilation, the one or more gas parameters, and/or the one or more breathing parameters may be determined one or more times for individual inhalations and/or exhalations in a series of breaths by subject 12.

The information determined by alveolar ventilation component 42 may be used for controlling pressure generator 14, stored in electronic storage 24, and/or used for other uses. In some embodiments, one or more determined parameters may be used by alveolar ventilation component 42 to further determine additional parameters. In some embodiments, the one or more gas parameters and/or breathing parameters may be related to one or more of rates (e.g., breath rate, flow rate), volumes (e.g., tidal volume, minute volume, etc.), pressures (e.g., inhalation pressure, exhalation pressure, etc.), other compositions (e.g., concentration(s)) of one or more constituent gasses, a gas temperature, a gas humidity, acceleration, velocity, acoustics, changes in a parameter indicative of respiratory effort by subject 12, and/or other parameters.

Adjustment component 44 is configured to cause pressure generator 14 to adjust the one or more ventilation parameters of the pressurized flow of breathable gas based on the determined alveolar ventilation, and/or other parameters. In some embodiments, adjustment component 44 is configured to cause pressure generator 14 to adjust the ventilation parameters of the pressurized flow of breathable gas via electronic communication with the valves, blower, motor (e.g., the servo controllers, valves, motors), and/or other components of pressure generator 14. In some embodiments, adjustment component 44 may be configured to determine one or more gain scaling terms and control pressure generator 14 based on the gain scaling terms.

In some embodiments, adjustment component 44 is configured to receive a target alveolar ventilation for subject 12 and cause pressure generator 14 to adjust the one or more ventilation parameters of the pressurized flow of breathable gas based on a difference between the determined alveolar ventilation and the target alveolar ventilation. The target alveolar ventilation may be received via user interface 22 and/or other components of system 10. The difference between the target alveolar volume and the determined alveolar volume is used to adjust the pressure support delivered to subject 12 on subsequent breaths and/or at other times. In some embodiments, adjustment component 44 is configured to adjust the one or more ventilation parameters within safety limits set by subject 12 and/or other users for individual parameters (e.g., via user interface 22).

Figure 3:
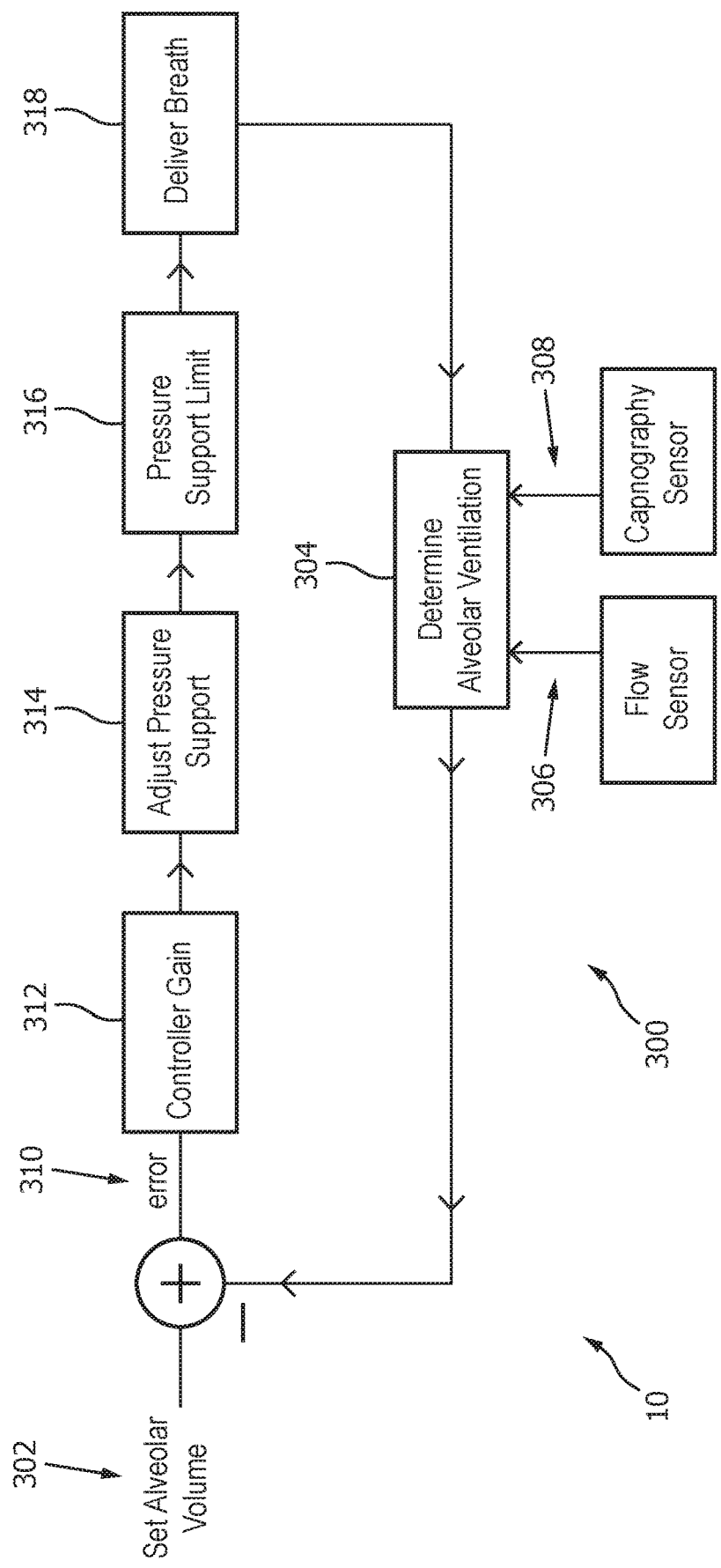
FIG. 3 illustrates a servo block diagram.

FIG. 3 illustrates a servo block diagram 300. FIG. 3 illustrates adjusting pressure support (e.g., the pressurized flow of breathable gas) provided to subject 12 (not shown in FIG. 3) to achieve a set (e.g., target) alveolar volume. As shown in FIG. 3, system 10 receives 302 a set (target) alveolar volume and determines 304 the alveolar ventilation of subject 12. As described above and shown in FIG. 3, the alveolar ventilation of subject 12 is determined based on output signals from sensors 18 (e.g., flow sensor 306 and capnography sensor 308) and/or other information. System 10 determines an error 310 between the target alveolar volume and the determined alveolar ventilation, determines a controller gain 312, and determines an adjustment for one or more ventilation parameters of the pressurized flow of breathable gas providing pressure support 314 (e.g., to reduce error 310). Finally, system 10 determines whether the adjustments are within safety limits 316 (and adjusts the parameters based on the safety limits if necessary) and then delivers a breath to subject 12.

Figure 4:
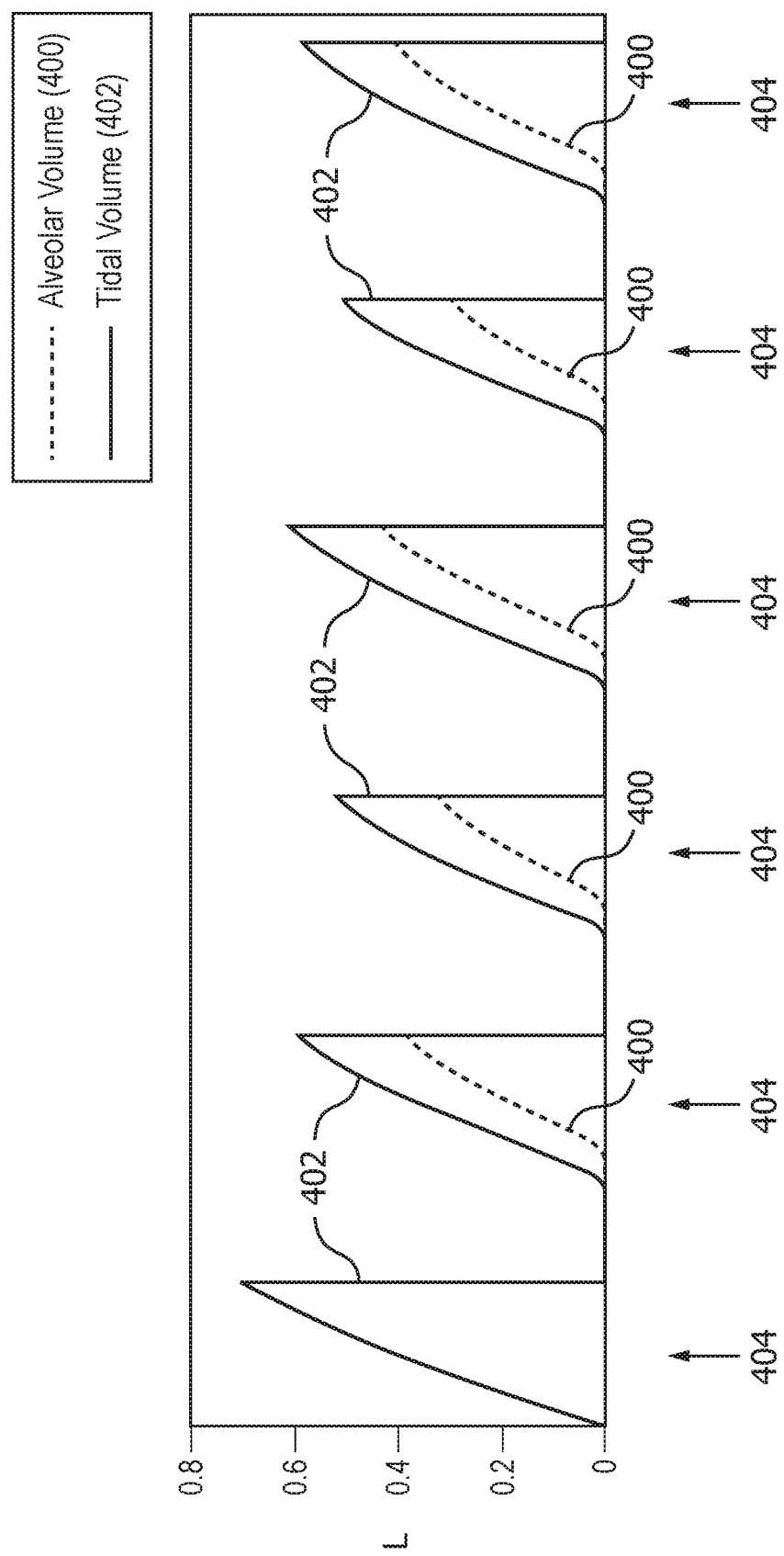
FIG. 4 illustrates tidal volume versus alveolar volume for individual breaths.

FIG. 4 illustrates the alveolar volume 400 compared to the tidal volume 402 for subject 12 (not shown in FIG. 4). Alveolar volume 400 shown in FIG. 4 was determined by system 10 as described above based on output signals from sensors 18 (not shown in FIG. 4) monitoring a healthy subject 12 breathing with a non-invasive interface. As shown in FIG. 4, alveolar volume 400 is lower than tidal volume 402 for each breath 404. System 10 (not shown in FIG. 4) is configured to control mechanical ventilation based on alveolar volume 400, unlike prior art systems which would control ventilation based on tidal volume 402.

Returning to FIG. 1, user interface 22 is configured to provide an interface between system 10 and subject 12 and/or other users through which subject 12 and/or other users provide information to and receive information from system 10. For example, user interface 22 is configured to receive entry and/or selection of control inputs (e.g., a target alveolar ventilation) from subject 12 and/or other users that specify control parameters for mechanical ventilation and/or other information. Other users may comprise a caregiver, a doctor, a decision maker, and/or other users. User interface 22 enables data, cues, results, and/or instructions and any other communicable items, collectively referred to as "information," to be communicated between a user (e.g., subject 12) and one or more of pressure generator 14, sensors 18, processor 20, electronic storage 24, and/or other components of system 10. Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 22 comprises a plurality of separate interfaces. In some embodiments, user interface 22 comprises at least one interface that is provided integrally with pressure generator 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function as described herein. Electronic storage 24 may be (in whole or in part) a separate component within system 10, or electronic storage 24 may be provided (in whole or in part) integrally with one or more other components of system 10 (e.g., user interface 22, processor 20, etc.).

Figure 5:
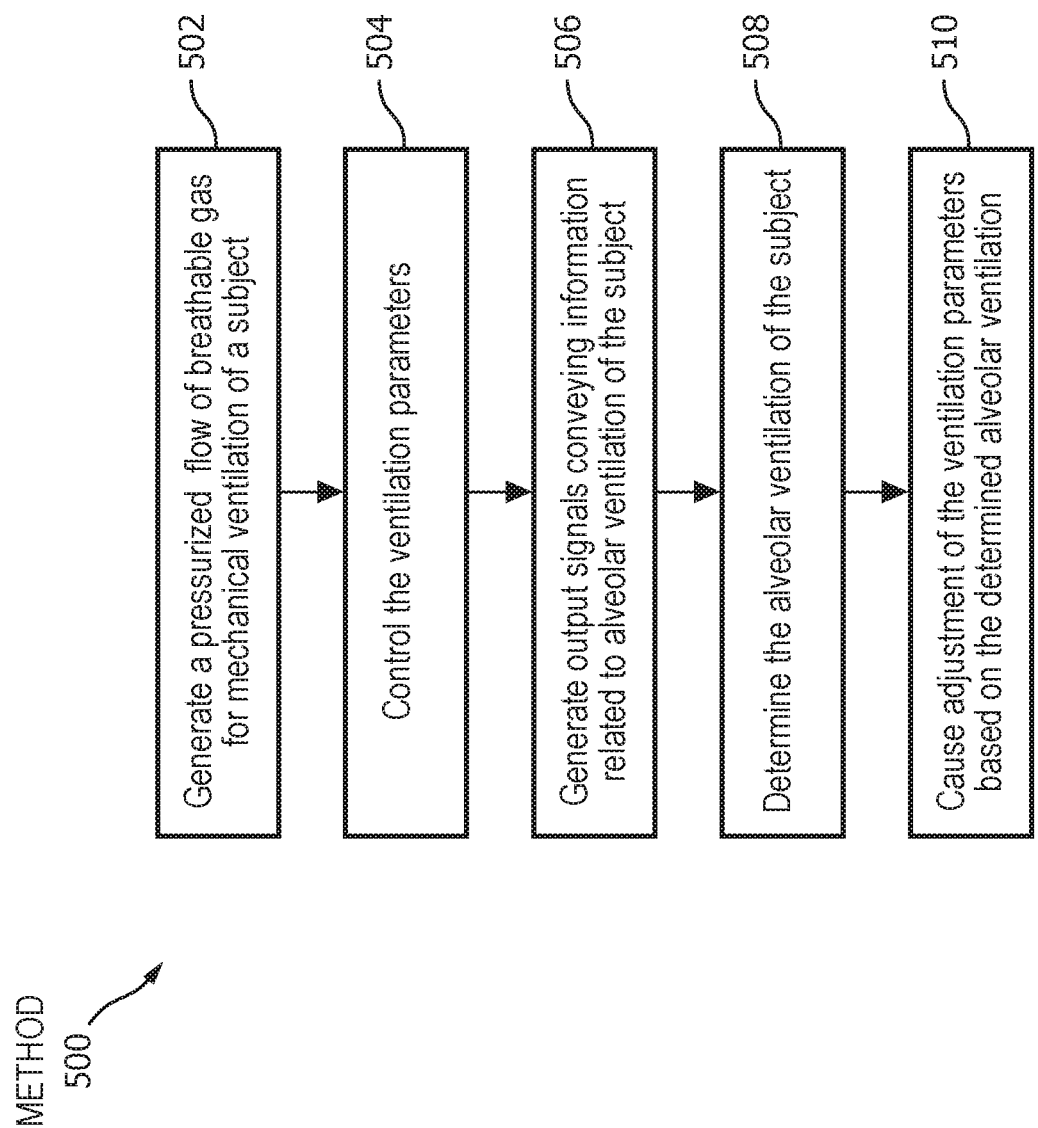
FIG. 5 illustrates a method for controlling a pressurized flow of breathable gas for delivery to a subject based on alveolar ventilation of the subject.

FIG. 5 illustrates a method 500 for controlling a pressurized flow of breathable gas for delivery to a subject with a mechanical ventilator system based on alveolar ventilation of the subject. The mechanical ventilator system comprises a pressure generator, one or more sensors, one or more hardware processors, and/or other components. The one or more hardware processors are configured by machine-readable instructions to execute computer program components. The computer program components include a control component, an alveolar ventilation component, an adjustment component, and/or other components. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, the pressurized flow of breathable gas is generated. In some embodiments, operation 502 is performed by a pressure generator the same as or similar to pressure generator 14 (shown in FIG. 1 and described herein).

At an operation 504, one or more ventilation parameters of the pressurized flow of breathable gas are controlled to promote and/or limit alveolar ventilation. The one or more ventilation parameters of the pressurized flow of breathable gas comprise one or more of breath rate, flow rate, pressure support positive end expiratory pressure (PEEP), tidal volume, minute volume, I:E ratio, and/or other parameters. In some embodiments, operation 504 is performed by a pressure generator the same as or similar to pressure generator 14 and/or a processor component the same as or similar to control component 40 (shown in FIG. 1 and described herein).

At an operation 506, output signals conveying information related alveolar ventilation of the subject are generated.

In some embodiments, generating output signals conveying information related to the alveolar ventilation of the subject comprises generating, with a flow rate sensor, output signals conveying information related to a flow rate of the pressurized flow of breathable gas, and generating, with a capnography sensor, output signals conveying information related to a concentration of $CO_2$ in the pressurized flow of breathable gas. In some embodiments, operation 506 is performed by sensors the same as or similar to sensors 18 (shown in FIG. 1 and described herein).

At an operation 508, alveolar ventilation of the subject is determined. The alveolar ventilation is determined based on the output signals and/or other information. In some embodiments, determining the alveolar ventilation of the subject based on the output signals includes determining an exhaled volumetric flow of $CO_2$ based on the flow rate information and the $CO_2$ concentration information, and integrating the exhaled volumetric flow of $CO_2$ during an expiratory phase of the subject. In some embodiments, operation 508 is performed by a computer program component the same as or similar to alveolar ventilation component 42 (shown in FIG. 1 and described herein).

At an operation 510, the pressure generator is caused to adjust the one or more ventilation parameters of the pressurized flow of breathable gas based on the determined alveolar ventilation. In some embodiments, operation 510 includes receiving a target alveolar ventilation for the subject and causing the pressure generator to adjust the one or more ventilation parameters of the pressurized flow of breathable gas based on a difference between the determined alveolar ventilation and the target alveolar ventilation. In some embodiments, operation 510 is performed by a computer program component the same as or similar to adjustment component 44 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A mechanical ventilator system configured to control a pressurized flow of breathable gas for delivery to a subject based on alveolar ventilation of the subject, the mechanical ventilator system comprising:
   a pressure generator configured to generate the pressurized flow of breathable gas for delivery to the subject, the pressure generator configured to control one or more ventilation parameters of the pressurized flow of breathable gas according to a prescribed mechanical ventilation therapy regime, wherein the one or more ventilation parameters of the pressurized flow of breathable gas comprise one or more of breath rate, flow rate, pressure support positive end expiratory pressure (PEEP), minute volume, or I:E ratio;
   one or more sensors configured to generate output signals conveying information related to the alveolar ventilation of the subject, wherein the one or more sensors comprise a flow rate sensor configured to generate output signals conveying information related to the flow rate of the pressurized flow of breathable gas, and a capnography sensor configured to generate output signals conveying information related to a concentration of $CO_2$ in the pressurized flow of breathable gas; and
   one or more hardware processors configured by machine-readable instructions to:
      synchronize the flow rate information and the $CO_2$ concentration information;
      determine the alveolar ventilation of the subject multiple times per inhalation and/or exhalation based on the synchronized flow rate and $CO_2$ concentration information; and
      cause the pressure generator to adjust the one or more ventilation parameters of the pressurized flow of breathable gas including one or more of the breath rate, the flow rate, the PEEP, the minute volume, or the I:E ratio based on the determined alveolar ventilation.

2. The system of claim 1, wherein the one or more hardware processors are further configured to receive a target alveolar ventilation for the subject and cause the pressure generator to adjust the one or more ventilation parameters of the pressurized flow of breathable gas based on a difference between the determined alveolar ventilation and the target alveolar ventilation.

3. The system of claim 1, wherein the one or more hardware processors are further configured such that determining the alveolar ventilation of the subject based on the output signals includes:
   determining an exhaled volumetric flow of $CO_2$ based on the synchronized flow rate and $CO_2$ concentration information; and
   integrating the exhaled volumetric flow of $CO_2$ during an expiratory phase of the subject.

4. The system of claim 1, wherein the one or more hardware processors are further configured such that determining the alveolar ventilation of the subject based on the output signals includes:
   synchronizing the flow rate information and the $CO_2$ concentration information with a deconvolution algorithm to reduce or eliminate effects of sensor delay;
   determining an exhaled volumetric flow of $CO_2$ based on the synchronized flow rate information and the $CO_2$ concentration information; and
   integrating the exhaled volumetric flow of $CO_2$ during an expiratory phase of the subject.

5. A method for controlling a pressurized flow of breathable gas for delivery to a subject with a mechanical ventilator system based on alveolar ventilation of the subject, the mechanical ventilator system comprising a pressure generator, one or more sensors, and one or more hardware processors, the method comprising:
   generating, with the pressure generator, the pressurized flow of breathable gas for delivery to the subject;

controlling, with the pressure generator, one or more ventilation parameters of the pressurized flow of breathable gas according to a prescribed mechanical ventilation therapy regime, wherein the one or more ventilation parameters of the pressurized flow of breathable gas comprise one or more of breath rate, flow rate, pressure support positive end expiratory pressure (PEEP), minute volume, or I:E ratio;

generating, with the one or more sensors, output signals conveying information related to the alveolar ventilation of the subject, wherein the one or more sensors comprise a flow rate sensor configured to generate output signals conveying information related to the flow rate of the pressurized flow of breathable gas, and a capnography sensor configured to generate output signals conveying information related to a concentration of $CO_2$ in the pressurized flow of breathable gas;

synchronizing, with the one or more hardware processors, the flow rate information and the $CO_2$ concentration information;

determining, with the one or more hardware processors, multiple times per inhalation and/or exhalation, the alveolar ventilation of the subject based on the synchronized flow rate and $CO_2$ concentration information; and causing, with the one or more hardware processors, the pressure generator to adjust the one or more ventilation parameters of the pressurized flow of breathable gas including one or more of the breath rate, the flow rate, the PEEP, the minute volume, or the I:E ratio based on the determined alveolar ventilation.

6. The method of claim 5, further comprising receiving, with the one or more hardware processors, a target alveolar ventilation for the subject and causing, with the one or more hardware processors, the pressure generator to adjust the one or more ventilation parameters of the pressurized flow of breathable gas based on a difference between the determined alveolar ventilation and the target alveolar ventilation.

7. The method of claim 5, wherein determining the alveolar ventilation of the subject based on the output signals includes:
  determining, with the one or more hardware processors, an exhaled volumetric flow of $CO_2$ based on the synchronized flow rate and $CO_2$ concentration information; and
  integrating, with the one or more hardware processors, the exhaled volumetric flow of $CO_2$ during an expiratory phase of the subject.

8. The method of claim 5, wherein determining the alveolar ventilation of the subject based on the output signals includes:
  synchronizing the flow rate information and the $CO_2$ concentration information with a deconvolution algorithm to reduce or eliminate effects of sensor delay;
  determining an exhaled volumetric flow of $CO_2$ based on the synchronized flow rate information and the $CO_2$ concentration information; and
  integrating the exhaled volumetric flow of $CO_2$ during an expiratory phase of the subject.

9. A mechanical ventilator system configured to control a pressurized flow of breathable gas for delivery to a subject based on alveolar ventilation of the subject, the mechanical ventilator system comprising:
  means for generating the pressurized flow of breathable gas for delivery to the subject, the means for generating the pressurized flow of breathable gas configured to control one or more ventilation parameters of the pressurized flow of breathable gas according to a prescribed mechanical ventilation therapy regime, wherein the one or more ventilation parameters of the pressurized flow of breathable gas comprise one or more of breath rate, flow rate, pressure support positive end expiratory pressure (PEEP), minute volume, or I:E ratio;
  means for generating output signals conveying information related to the alveolar ventilation of the subject, wherein the means for generating output signals comprise a flow rate sensor configuration to generate output signals conveying information related to a flow rate of the pressurized flow of breathable gas, and a capnography sensor configured to generate output signals conveying information related to a concentration of $CO_2$ in the pressurized flow of breathable gas;
  means for synchronizing the flow rate information and the $CO_2$ concentration information;
  means for determining the alveolar ventilation of the subject multiple times per inhalation and/or exhalation based on the synchronized flow rate and $CO_2$ concentration information; and
  means for causing the means for generating the pressurized flow of breathable gas to adjust the one or more ventilation parameters of the pressurized flow of breathable gas including one or more of the breath rate, the flow rate, the PEEP, the minute volume, or the I:E ratio based on the determined alveolar ventilation.

10. The system of claim 9, further comprising means for receiving a target alveolar ventilation for the subject and causing the means for generating the pressurized flow of breathable gas to adjust the one or more ventilation parameters of the pressurized flow of breathable gas based on a difference between the determined alveolar ventilation and the target alveolar ventilation.

11. The system of claim 9, wherein determining the alveolar ventilation of the subject based on the output signals includes:
  determining an exhaled volumetric flow of $CO_2$ based on the synchronized flow rate and $CO_2$ concentration information; and
  integrating the exhaled volumetric flow of $CO_2$ during an expiratory phase of the subject.

12. The system of claim 9, wherein determining the alveolar ventilation of the subject based on the output signals includes:
  synchronizing the flow rate information and the $CO_2$ concentration information with a deconvolution algorithm to reduce or eliminate effects of sensor delay;
  determining an exhaled volumetric flow of $CO_2$ based on the synchronized flow rate information and the CO2 concentration information; and
  integrating the exhaled volumetric flow of $CO_2$ during an expiratory phase of the subject.

* * * * *